US008636259B2

(12) United States Patent  (10) Patent No.: US 8,636,259 B2
Manke et al.  (45) Date of Patent: Jan. 28, 2014

(54) ADJUSTABLE CARRIAGE HOLDER FOR SUPPORT APPARATUS

(75) Inventors: Scott G. Manke, Sun Prairie, WI (US); Brian A. Harbrecht, Janesville, WI (US); Anthony Charles Grabski, Blue Mounds, WI (US); Robert Charles Mierendorf, Verona, WI (US); James L. Rane, Madison, WI (US)

(73) Assignee: Semba Biosciences, Inc., Madison, WI (US)

( * ) Notice: Subject to any disclaimer, the term of this patent is extended or adjusted under 35 U.S.C. 154(b) by 287 days.

(21) Appl. No.: 13/182,097

(22) Filed: Jul. 13, 2011

(65) Prior Publication Data

US 2012/0012719 A1  Jan. 19, 2012

Related U.S. Application Data

(60) Provisional application No. 61/364,253, filed on Jul. 14, 2010.

(51) Int. Cl.
*F16M 13/00* (2006.01)

(52) U.S. Cl.
USPC ........ 248/512; 248/523; 248/125.7; 248/912; 211/85.13; 211/78

(58) Field of Classification Search
USPC .................. 211/68, 70, 70.4, 78, 85.13, 60.1; 248/511, 512, 513, 519, 521, 523, 535, 248/74.2, 113, 125.7, 425, 186.2, 349.1, 248/912
See application file for complete search history.

(56) References Cited

U.S. PATENT DOCUMENTS

| | | | | | |
|---|---|---|---|---|---|
| 1,332,086 | A | * | 2/1920 | Van Sickles | 248/113 |
| 1,691,035 | A | * | 11/1928 | Adams | 108/141 |
| 1,736,290 | A | * | 11/1929 | Schiff | 248/113 |
| 1,915,725 | A | | 6/1933 | Fisher | |
| 2,084,249 | A | * | 6/1937 | Will | 108/148 |
| 2,269,790 | A | | 1/1942 | Sherrill | |
| 2,376,955 | A | * | 5/1945 | Ball | 211/60.1 |
| 2,499,945 | A | | 3/1950 | Burrell | |
| 2,512,622 | A | * | 6/1950 | Fish | 206/317 |
| 2,516,965 | A | | 8/1950 | Dresser | |
| 3,161,393 | A | * | 12/1964 | Swanson | 248/113 |
| 3,893,813 | A | | 7/1975 | Johnson | |
| 4,591,123 | A | * | 5/1986 | Bradshaw et al. | 248/179.1 |
| 4,688,685 | A | * | 8/1987 | Brace | 211/70.5 |
| 7,431,259 | B2 | * | 10/2008 | Tung | 248/521 |
| 7,575,676 | B2 | | 8/2009 | Prentice et al. | |
| 7,676,983 | B2 | * | 3/2010 | Jenkins | 43/21.2 |
| 2002/0179783 | A1 | * | 12/2002 | Kim | 248/122.1 |
| 2003/0173473 | A1 | * | 9/2003 | Mackay et al. | 248/125.7 |
| 2005/0252871 | A1 | * | 11/2005 | Le Roux | 211/70.6 |

* cited by examiner

*Primary Examiner* — Bradley Duckworth
(74) *Attorney, Agent, or Firm* — Foley & Lardner LLP

(57) ABSTRACT

A carriage holder for support of an apparatus includes identical upper and lower support plates having on their outer edge a number of indentations corresponding to the number of apparatus to be supported, said indentations providing aligned radial horizontal grasping surfaces on one side of said apparatus. The carriage holder also includes a series of vertical spring pivot pins joining said upper and lower support plates, adjacent to each said indentation, each such pin bearing a torsion spring loaded retractable clamp member to provide grasping surfaces in retracted position opposite to the grasping surfaces of said indentations. The carriage holder also includes an unobstructed aperture in each of said aligned support plates for mounting said carriage holder on a shaft. The carriage holder further includes a locking mechanism to hold said carriage in a fixed position on the shaft.

6 Claims, 11 Drawing Sheets

ADJUSTABLE CARRIAGE HOLDER FOR SUPPORT APPARATUS

CROSS-REFERENCE TO RELATED PATENT APPLICATIONS

The present application claims priority to U.S. Provisional Patent Application No. 61/364,253 filed Jul. 14, 2010, the contents of which are incorporated herein by reference in their entirety.

BACKGROUND

In laboratories, it is common practice to use many devices to secure tools in a fixed position. Various types of mechanical clamps, rings, and other grasping implements have been devised to immobilize burettes, funnels, tubes, flasks, and chromatographic columns so they can be used in vertical operation.

A conventional clamping device is disclosed in U.S. Pat. No. 2,269,790. It consists essentially of two functional parts, as do clamping devices generally. One functional part consists of means for grasping the article to be suspended, and the other to affix the vertically held article to a vertical shaft. In '790, both functions are performed by wire bent into the shape of the intended article, and the second by a spring-like wire coil having a bent diameter slightly less than the article, with wire tabs that top of base and top of the coil. Compression of the tabs enlarges the coil diameter permitting insertion of the article. Releasing the tabs compresses the coil against the article, thus firmly folding it in place.

U.S. Pat. No. 1,915,725 discloses a burette holder in which burettes or other cylindrical articles are maintained in position against a frame cavity by applying pressure to opposite side of the cylindrical article with a movable spring-loaded armature. This design allows pressure from one source to impact the cylinder at two or more vertical points on the frame, ensuring vertical disposition of the cylinder. U.S. Pat. No. 2,499,945 discloses a similar apparatus having a single horizontally disposed spring that applies pressure to the cylinder from two such armatures simultaneously. Securing the cylinder-mounting portion of the frame at the ends of the apparatus also provides adequate working space between the cylinder and the support shaft.

The frame is adjustably secured to the support shaft by a vertical collar embracing the shaft and fixed by means of a set screw, which tightens the collar portion to the shaft. This is a common feature of many pieces of laboratory support apparatus, as shown also in U.S. Pat. Nos. 2,269790, 3,893,813, 2,516,965, and 2,499,945. This feature is adequate for laboratory applications because burettes, funnels, and chromatography columns are not heavy objects. However, a set screw is not satisfactory where much weight is involved since there the amount of torque force that can be transmitted by a set screw is limited.

Other types of clamping devices have been disclosed. U.S. Pat. Nos. 2,269790 and 3,893,813 describe grasping apparatus in which both sides of a cylinder are held by separate movable grasping arm. In '813, the apparatus has a frusto-conical adjusting cam wedge such that a spindle knob is helically displaced one way or the other to bear against or retreat from the chambered portions of the arms to open or close a pair of grasping tongs. In '790 clamp arms pivot when a nut is tightened on a threaded portion of a stud, thereby allowing the arms to move towards and away from each other about a common axis.

Finally, U.S. Pat. No. 7,575,676 discloses a square clip device whose interface portion secures the apparatus to a platform, and a second clip device that secures an HPLC column to a correspondingly square shaft. In some embodiments the frictional resistance to displacement of the clip along the shaft is enhanced by placement of upper and lower tooth-like elements which can interact with a securing device having at least one dentated track along its outer surface.

SUMMARY

A carriage apparatus is provided capable of holding one or a plurality of tubes, burettes, chromatography columns, or other vertically disposed generally cylindrical apparatus. Described herein is a clip type holder for quick and easy engagement and disengagement of such apparatus, and to suspend same adjustably but securely on a shaft. The holder is adapted so that the clip can be operating with hand while the other hand is holding and adjusting the position of the apparatus to be engaged. While the novel carriage may operate as a single unit, many operations require multiple units, so that an array of units on a single carriage is desirable. In particular, the subject matter described herein has efficacy in suspending a number of chromatography columns used simultaneously in Simulated Moving Bed Chromatography (SMBC).

Another object is to provide a locking mechanism which holds the carriage at a fixed position on a shaft, so that movement vertically up or down the shaft is retrained, but the carriage may be freely rotated or turned about its vertical axis. The locking mechanism also provides a release that then allows the carriage position to be adjusted freely along the shaft. In a further embodiment, a variation in configuration of the locking mechanism locks the carriage in one direction, but permits free movement in the other.

A carriage holder for support of one or a plurality of substantially cylindrical apparatus comprises upper and lower support plates having on their outer edge a number of indentations corresponding to the number of apparatus units to be supported. These indentations are aligned to provide radial horizontal grasping surfaces on side of the supported apparatus. The upper and lower support plates are aligned so that their respective indented grasping surfaces form two contact zones on the apparatus in vertical disposition.

There are a series of vertical spring pivot pins joining the upper and lower support plates in alignment. Each pivot pin bears a torsion spring retractable clamp member to provide grasping surfaces opposite to the grasping surfaces of the indentations. The torsion spring is immobilized by restraining means to prevent rotation thereof when the torsion spring is retracted. This maintains the apparatus in the grip of the grasping surfaces of the support plate indentations and the clamp member. There is also an unobstructed aperture in each of the aligned support plates in each of the aligned support plates for mounting the carriage holder in a fixed position on the support shaft. In addition, there is locking means to hold the carriage in a fixed position along the support shaft.

In one embodiment, there is provided a locking means for holding a platform plate, including a carriage holder, in an adjustable fixed position, where the locking means includes a locking lever having handle and body portions containing an aperture larger than the diameter of the shaft to fit over the shaft. There are tabs located laterally between the aperture and the handle. Bores spaced horizontally in the locking lever on the handle side of the lever between the aperture and the end of the lever, and a second bore situated on the handle side of the aperture.

Stabilizing pins extend between the upper and lower support plates through these bores which are disposed to guide a force means applied in orientation to the locking lever to urge and maintain it in locked position. There are mounting blocks affixed to the platform plate on either parallel side of the locking lever containing bushings to accommodate and receive the tabs of the locking lever, to provide an axis of rotation to the lever. The locking position is attained when the rim of the aperture is rotated by the force means into a contact engagement zone with the shaft. The force applied to the locking lever is great enough to prevent slippage of locking means on the shaft given the weight bearing load of the platform, but not so great as to impede axial rotation of the platform about the shaft.

DETAILED DESCRIPTION

Described herein is a carriage holder for a substantially cylindrical apparatus that performs two functions, namely, to easily engage by gripping action such apparatus and disengaging it in a single motion. The apparatus is normally suspended for vertical use, so that suspension means allows the carriage holder to be mounted on a vertical shaft and secured in a fixed position, which can be varied at will. The apparatus may also have an optional support plate to provide additional sturdiness and fidelity to alignment along a vertical axis.

Figure 1:
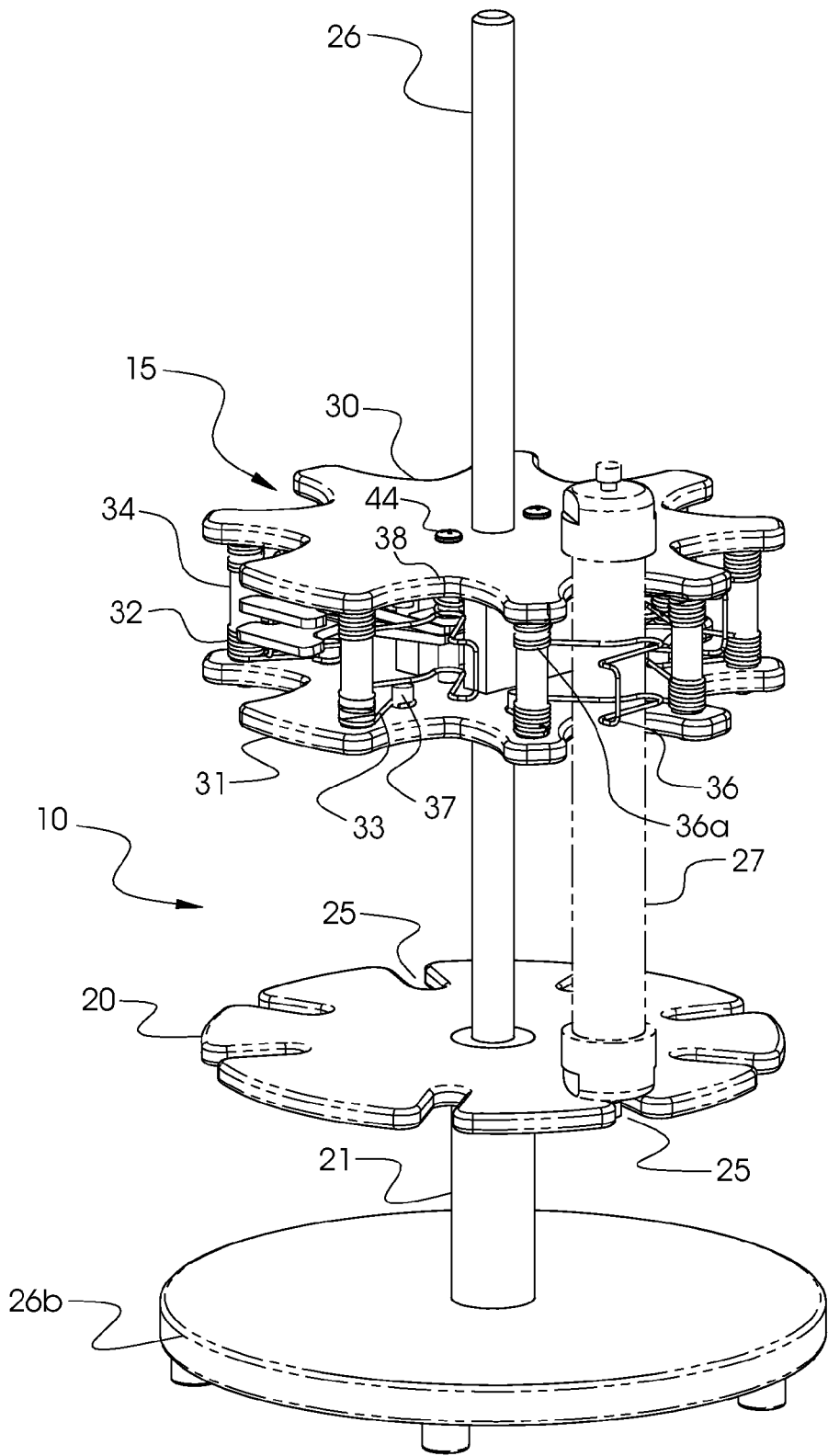
FIG. 1 is a perspective drawing of a complete apparatus support system showing a carriage holder assembly, an option base support member with sleeve, and a mounting shaft.

FIG. 1 shows the general configuration of a complete carriage holder system 10. It comprises a carriage holder assembly 15, an optional column support plate 20, a base plate 26b and a mounting shaft 26. The carriage holder assembly 15 comprises in its simplest form, an upper support plate 30 and a lower support plate 31. These plates have a series of indentations 38 whose vertical surfaces, when aligned as shown, provide a double seating surface for a cylindrical apparatus (dotted lines, 27). The number of indentations corresponds to the capacity of the holder assembly for holding apparatuses. The upper support plate 30 and the lower support plate 31 are joined by a series of vertical spring pivot pins 34. These may affixed to the plates by press fittings into recessed cavities in the lower surface of the upper plate and the upper surface of the lower plate. The connection can be further reinforced by inserting screws into the pins top and bottom through the plates (not shown).

Each pivot pin bears a retractable torsion spring member 36 having a vertically oriented spring 32 situated at the top and bottom of the pivot pins 34 connected by a torsion arm 36. The spring portions 32 of the torsion spring member 36 are anchored by a wire extension 33 forming a loop fitting over an anchor block 37. This prevents rotation of the spring when the torsion arm 36 is retracted to accommodate a cylindrical apparatus 27. Immobilization of the spring portions 32 may be obtained by other methods, such as gluing, or a set screw placed over the open end of the spring portions and embedded in the vertical spring pivot pins.

Figure 4:
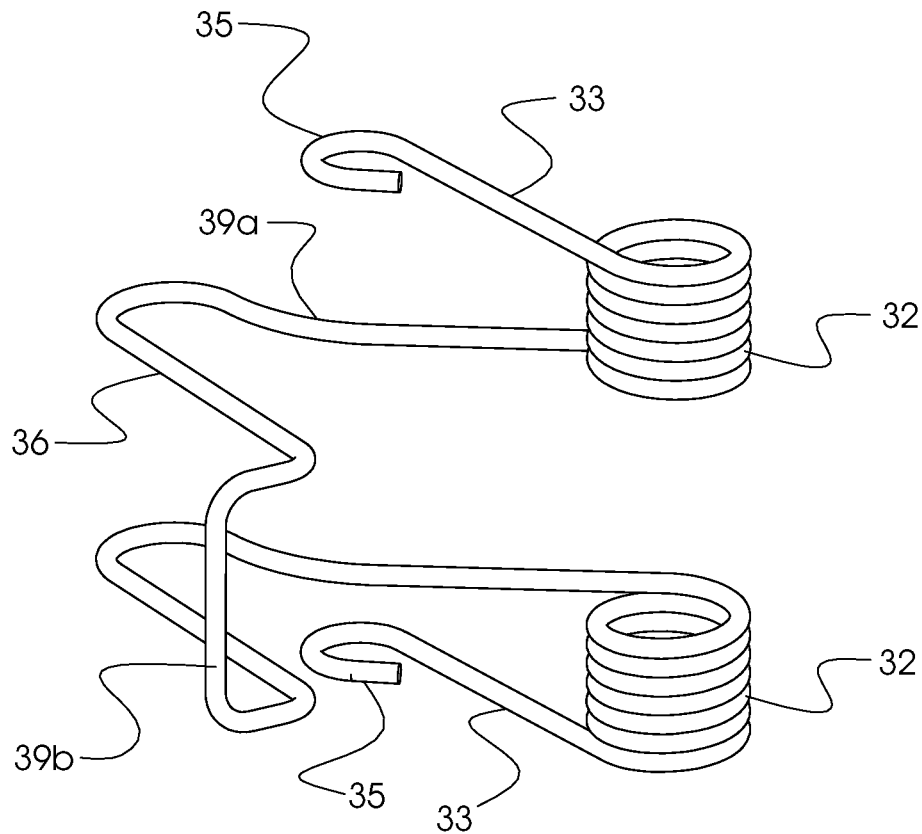
FIG. 4 is a perspective view of the retractable torsion spring member.

FIG. 4 illustrates the torsion spring member 36 in greater detail. The member is formed from a single strand of wire. At each end is a loop 35, shaped to fit around an anchor block, and a short extension 33. Next a coil portion 32 is formed. Note the coils at each respective end are wound in opposite directions (clockwise and counterclockwise), so that each (when anchored) imparts a force in the same direction towards the object to be held. The torsion arm 36 has a curved region 39a adapted to intercept the outer surface of the cylindrical apparatus at approximately a 180 degree angle from the contact zone of the support plate indentation (FIG. 1 38). The two halves of the spring member are connected by a handle portion 39b. It is shaped to optimize mechanical leverage in retracting the torsion spring member with one hand and facilitates insertion of small apparatus with the other.

Figure 2:
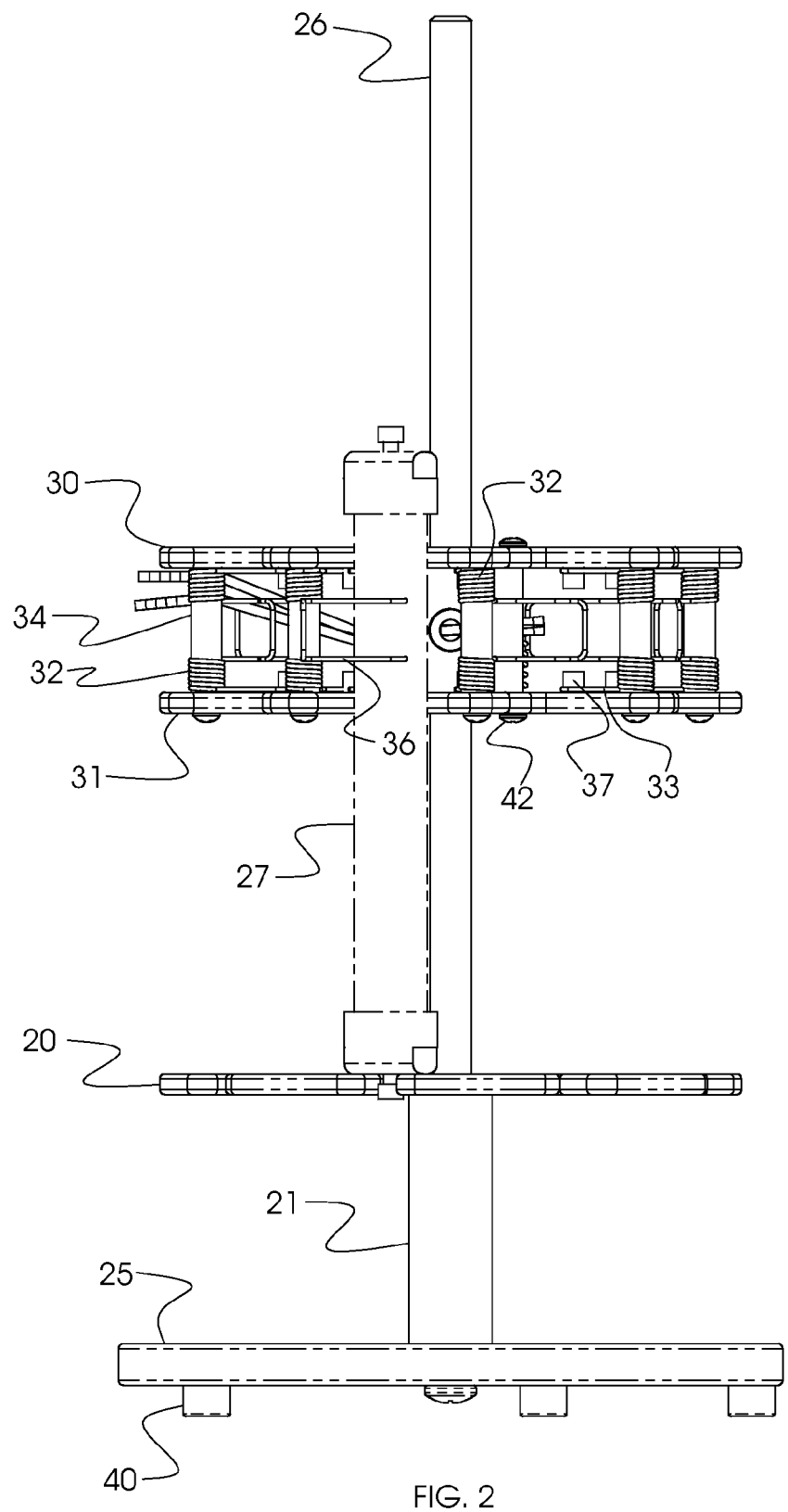
FIG. 2 is a side view of the complete apparatus depicted in FIG. 1.
Figure 3:
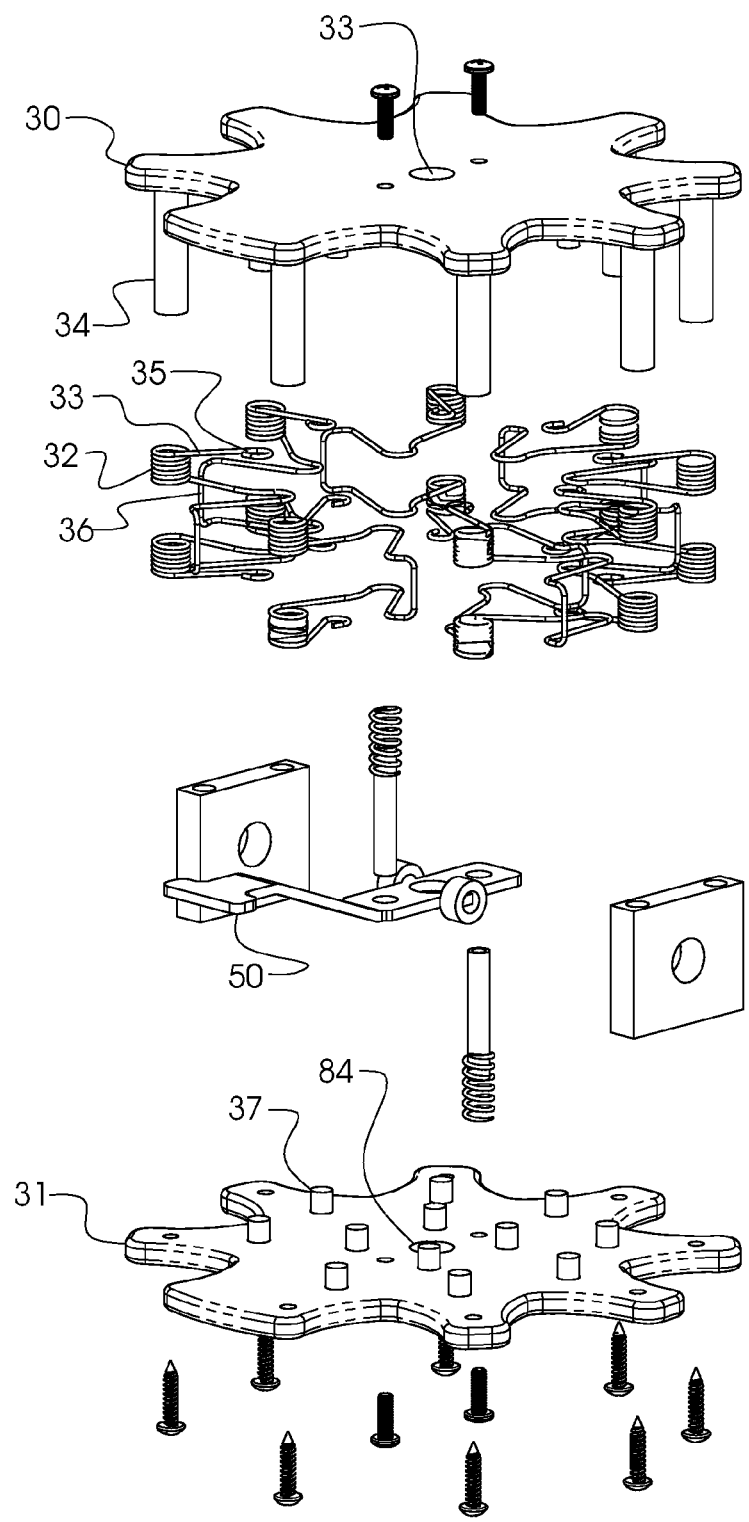
FIG. 3 is a two dimensional double exploded perspective view without the support shaft.

FIGS. 1 and 2 illustrate other features of the complete apparatus support system. The column support plate 20 is of a size conforming to that of the carriage hold assembly support plates 30 and 31. The column support plate 20 has a series of notches 25 centered in alignment under the indentations of the upper and lower support plates 30 and 31 of the carriage. This plate is generally only used when the cylindrical apparatus is a chromatography column. Since chromatography columns have an opening at the bottom of the column, the notches 25 facilitate egress of liquid from the column. As shown in the illustrative embodiment, the column support plate 20 is fitted to a sleeve 21, which slides over the shaft 26 so that it comes to rest at a fixed height above a base plate 26b. The base plate 26b is also an optional feature. The shaft could be inserted directly into an accommodating bore in a table top or lab bench.

The locking mechanism is an important aspect of the subject matter described herein. The carriage assembly 15 is designed to have an unobstructed generally central aperture 84 through which the shaft 26 supports the carriage assembly 15 by locking its position on the shaft. It is an advantage that the locking mechanism be releasable so that the position of the carriage can be varied at will to accommodate cylindrical apparatus of different lengths.

The locking mechanism operates on the principle that if a substantially flat sheet containing an aperture larger than the diameter of a shaft is inserted onto the shaft, in level position (90 degrees with respect to angle of the shaft), the sheet can be readily moved up and down the shaft with no resistance. However, if the sheet is tilted so that the edge of the aperture comes to contact with the shaft, it has a braking effect., because of the frictional forces generated thereby. If the aperture is a circle, there will be two zones of contact with the shaft, separated by 180 degrees, one on the upper edge of the aperture, and the other on the lower edge of the aperture. If the aperture is an egg-shaped irregular ellipse, there will be only one point of contact, assuming the distance of tilt is limited to the point of first contact. In this instance, there will be braking in one direction of travel, but free movement in the other.

Figure 6A:
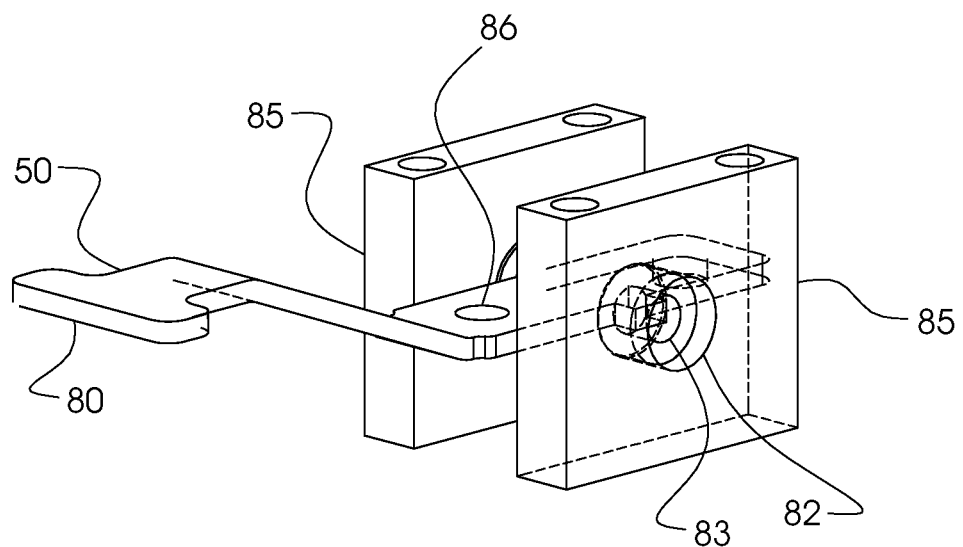
FIGS. 6A and 6B are isometric views of the locking lever assembly elements.
Figure 6B:
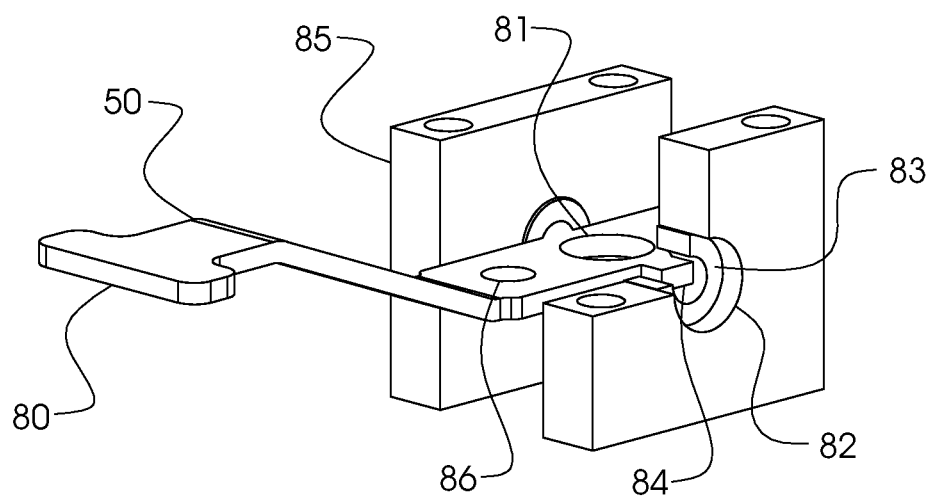

The foregoing principles have been applied to the locking mechanism of the present subject matter. FIG. 6B shows the mechanical components of the locking system, comprising a locking lever 50 having a handle portion 80, an aperture 81 which is intended to be mounted on a mounting shaft of lesser diameter, a bore 86 to receive a stabilizing pin, and tabs 84 inserted into a bushing 83 pressed into a bore 82 contained in a mounting block 85. The locking assembly is symmetrical with tabs on both sides of the locking lever, and each fitted into a bushing in the mounting blocks on both sides of it, to provide a pivot point for movement of the locking lever. FIGS. 6A and 6B show the locking lever in the open position so that the assembly would move freely in either direction on a shaft. The term "tabs" means any protuberance from the body of the locking lever that can create a pivot point. Tab is understood to mean also a welded circular hub inserted into a movable bearing or a rounded projection such as an axel.

Figure 5:
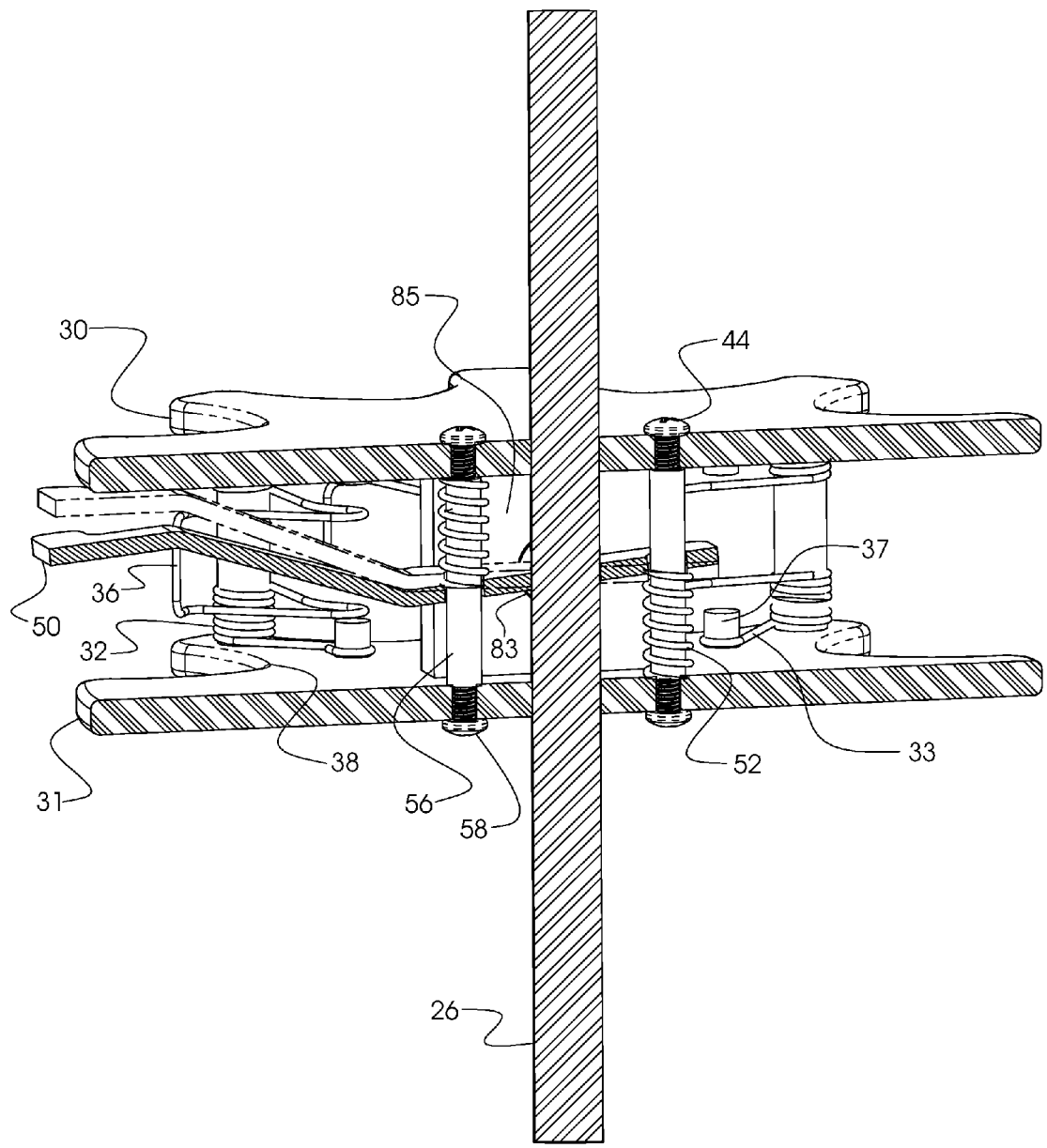
FIG. 5 is a frontal sectional view of a portion of the carriage holder showing the locking lever assembly in relation to the clamping mechanism.

FIG. 5 illustrates the locking mechanism in relation to other components of the carriage assembly 15 to which it is fitted. The locking lever 50 is shown in a side view in locked position. It is apparent that there is a slight upward tilt of the lever, so that the upper and lower edges of the aperture 81 are in braking engagement with the shaft 26. There are bores (not shown) on the body portion of the locking lever 50, through which pass vertical stabilizing pins 56, on either side of the aperture 81 and secured (shown here by threaded screws 44) in the upper and lower support plates 30 and 31 of the carriage assembly. In the illustrative embodiment the stabilizing pin bores are equidistant from the aperture 81, but they can be of different distances and of varying distance from the aperture 81 depending how much mechanical advantage is desired. As shown, the stabilizing pins 56 also act as guides for a spring 52 positioned between the upper and lower support plates 30 and 31 and the upper and lower surfaces of the locking lever 50 respectively. By virtue of the spring force exerted on both sides of the pivot point, the locking lever 50 is urged into locking engagement with the shaft 26. To release the lock, the operator need only pull up the locking lever 50 against the force of the springs to break engagement contact between the lever and shaft.

The force applied against the locking lever is shown in an illustrative embodiment as spring force. For laboratory scale equipment this is inexpensive and practical. However, in principle the locking mechanism could be used in any number of larger scale situations where the position of any platform moving on a shaft needs to be secured at fixed locations. As the platform advances in the permissive direction, backwards slippage is thereby prevented. The force in such instances may be supplied by pneumatic- and hydraulic-driven pistons, solenoids, and the like, instead of springs.

Figure 7:
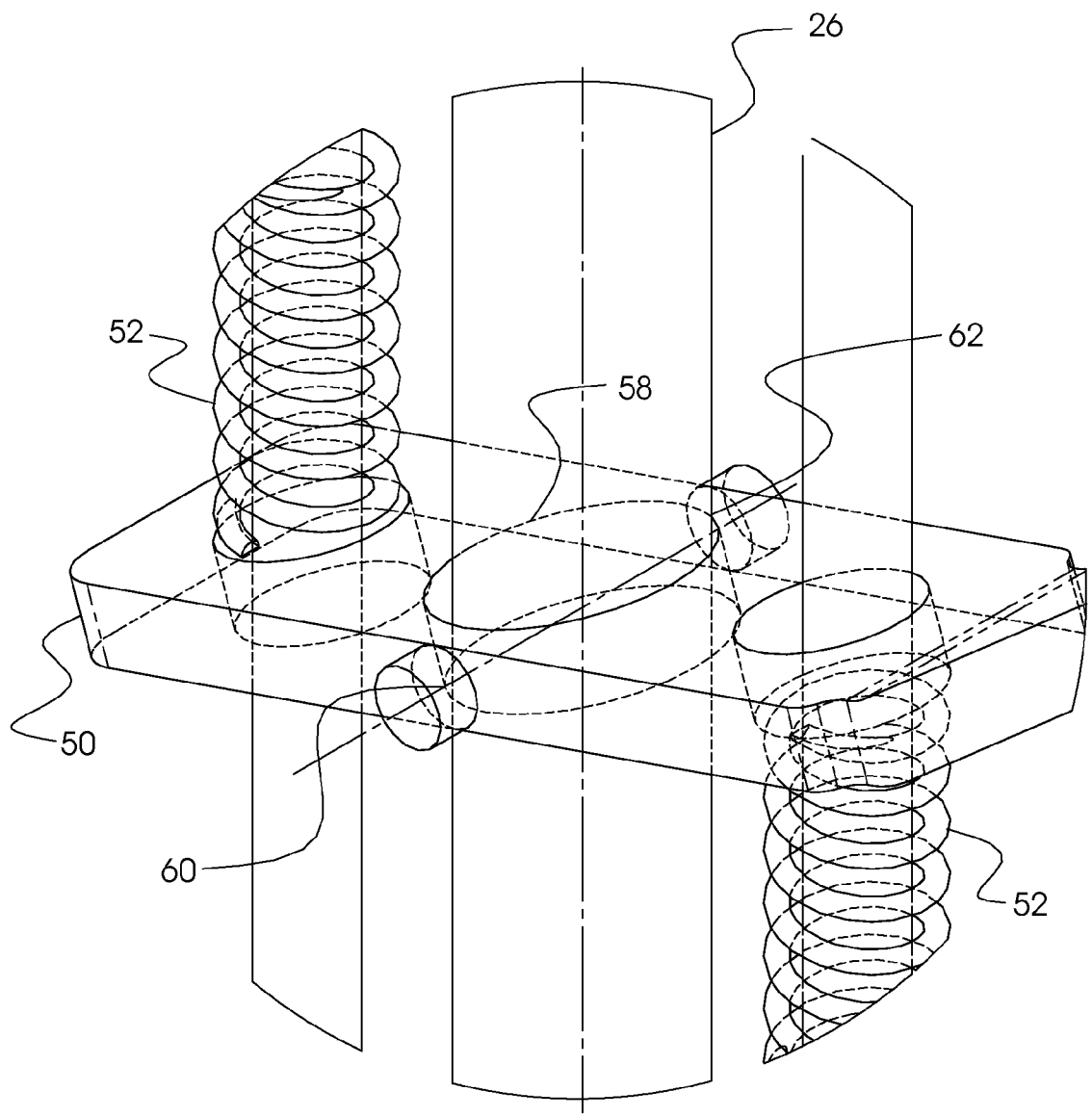
FIG. 7 is a perspective view and partial schematic of the locking device showing the locked position.
Figure 8:
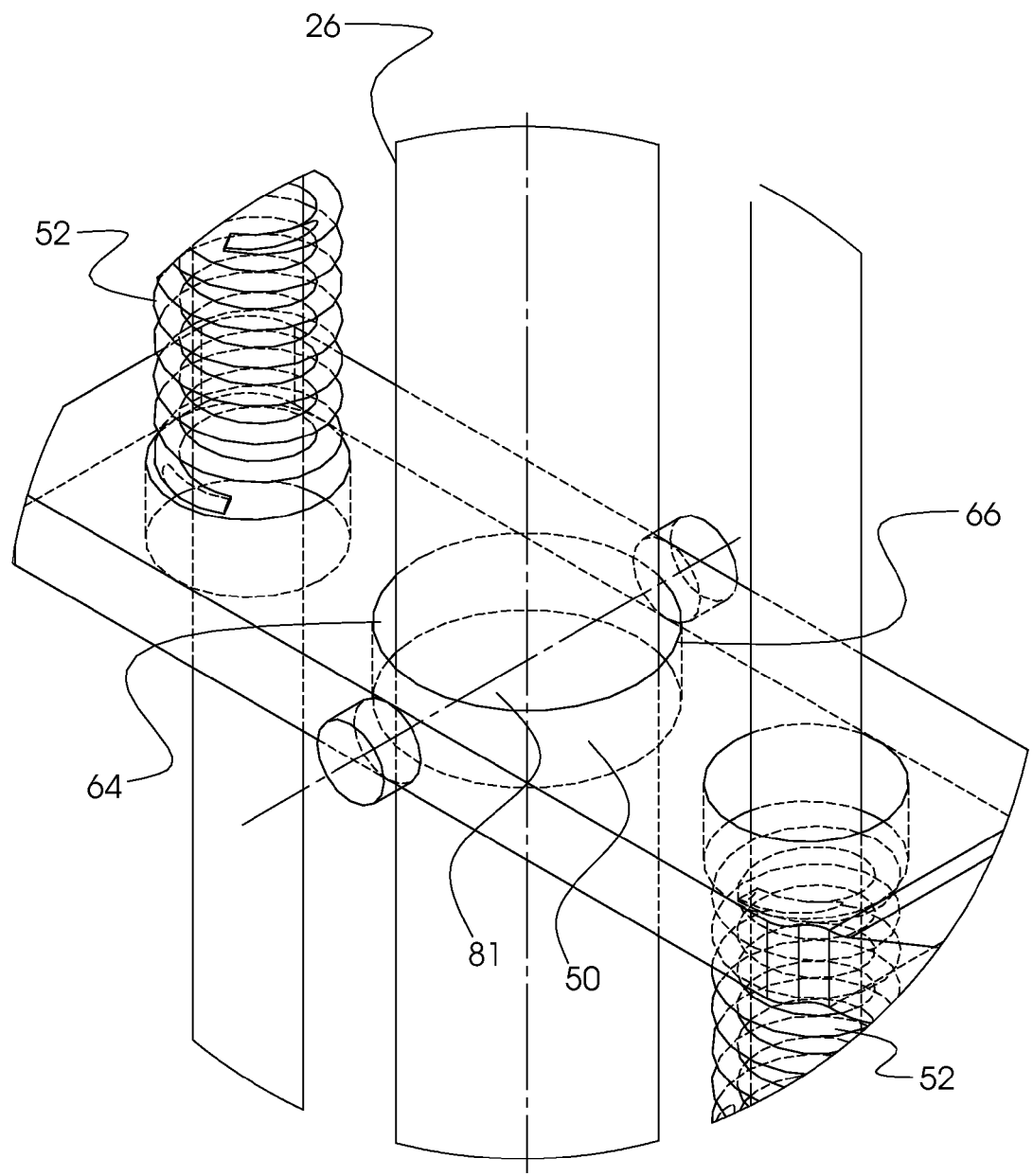
FIG. 8 is a perspective and partial schematic of the locking device showing the lock release position of the locking lever.

FIG. 7 is a schematic further showing the contact zone 60 between the locking lever 50 and the shaft 26 in tilted position. The diagram also shows the above and below configuration of the torsion screws 52. FIG. 8 is a replica of FIG. 7, showing the locking lever 50 in release position, and further demonstrating the clear gap 66 between the aperture 81 and the shaft 26, allowing free upward and downward movement without resistance.

In an alternative embodiment, the edge or edges of the aperture 81 may be beveled at an angle complementary to the angle of incidence of the locking level 50 and the shaft 26, so that the surface area of the contact zone 60 is enhanced by frictional contact resistance up to the width of the locking lever 50, or a portion thereof. This creates increased resistance to displacement of the carriage under vertical forces, against the carriage or platform, and provides an advantage to platforms having large weight-bearing applications. Failure limitations are determined by the type and strength properties of the materials comprising the locking lever and shaft, and less on the mechanical integrity of the locking mechanism.

Figure 9:
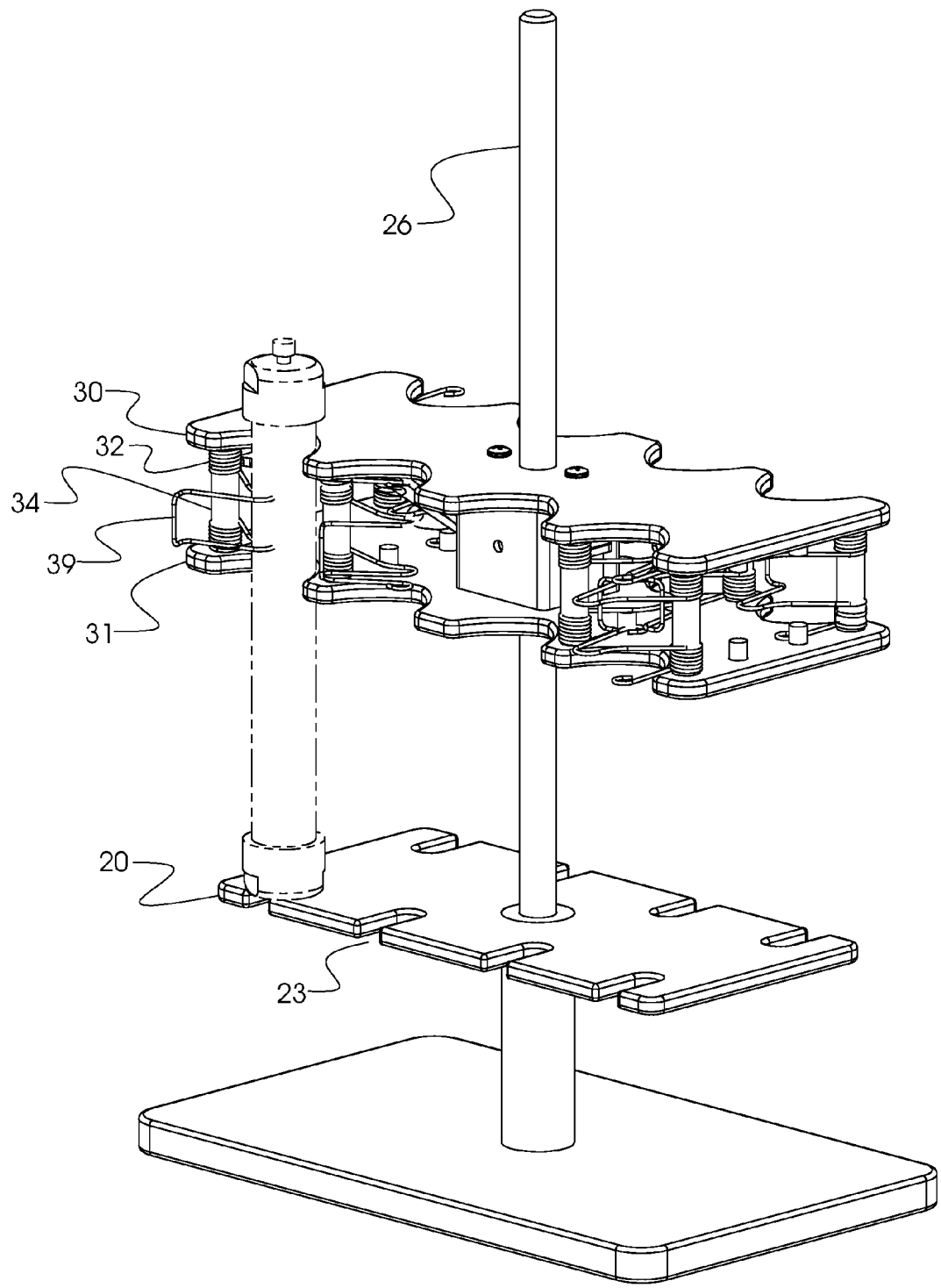
FIG. 9 is a perspective drawing of the carriage holder as a linear array of apparatus holding stations.

FIG. 9 is a drawing of the eight holding stations in linear array rather the circular configuration depicted in FIG. 1. This embodiment is otherwise identical, as to its structural and functional features, but illustrates the various special configurations the carriage holder may take. This particular embodiment has efficacy where bench space is narrow and will not accommodate the circular version. Note that because the same principles apply, in loading the apparatus stations, the rectangular carriage is rotatable without compromising the vertical position on the shaft 26, because the locking forces, as for the circular unit, are much greater than rotational resistance.

Figure 10:
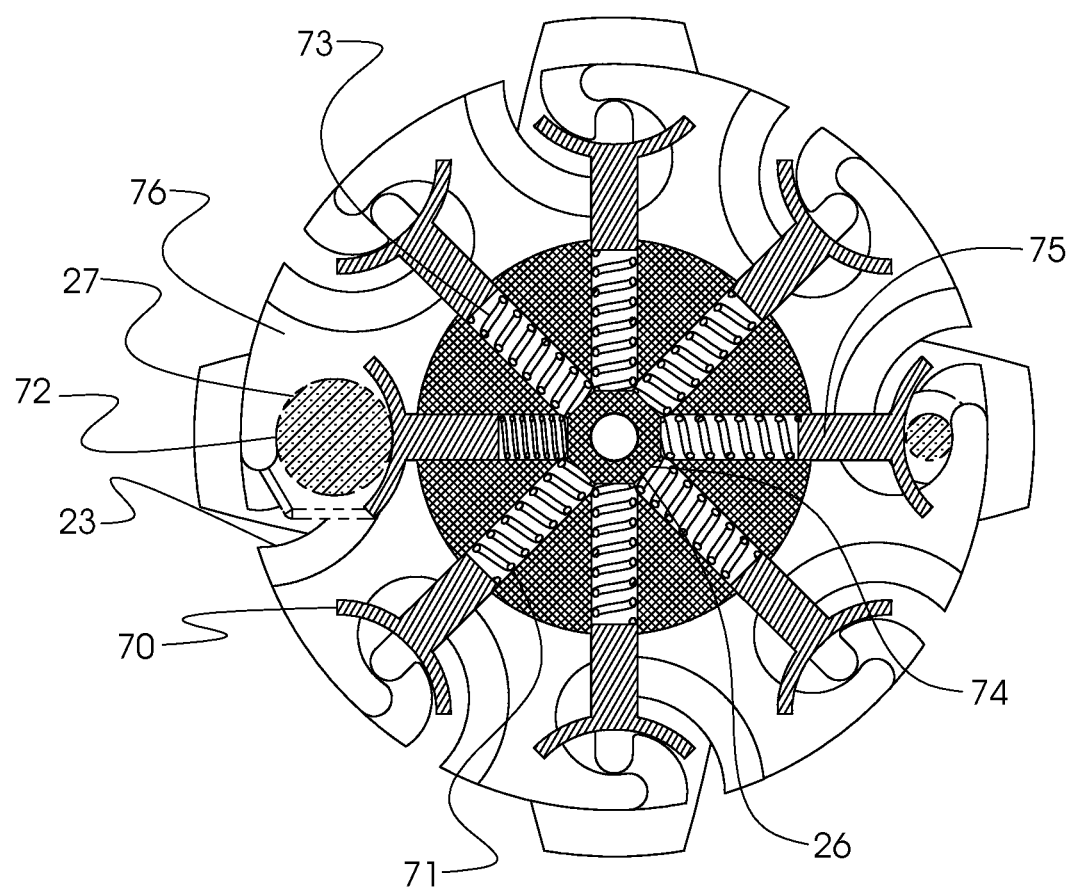
FIG. 10 is a top view of an alternative embodiment of the holder carriage showing a horizontal spring-loaded piston drive for a clamping mechanism.

FIG. 10 is an alternate embodiment utilizing a spring loaded 73 piston-type plunger 75 to force one side of a cylindrical apparatus against a fixed complementary surface 72 on a support plate 76. A vertical cylindrical apparatus 27 is compressed between the curvature vertical surface of a jaw portion 70 of the plunger 75.

EXAMPLE

Maximum Lever Rotation as a Function of Variation of Hole and Shaft Diameter

Introduction

The purpose of this discussion is to describe how the maximum rotation angle of the Vertical Release Lever is a function of the difference in diameters of the central hole in the Vertical Release Lever and the outer diameter of the Vertical Shaft.

Assumptions

This analysis was made on the existing geometry of the patent prototype, meaning the Vertical Shaft is assumed to have a circular cross section. The central hole in the Vertical Release Lever is also assumed to be circular. In practice, the Vertical Shaft may be non-circular, which may affect the relationship described in this analysis.

Methodology

This analysis was modeled in SolidWorks using the geometry of the existing patent prototype. The experimental method assumed the Vertical Shaft outer diameter was fixed at ½-inch and the central hole in the Vertical Release Lever was enlarged by several arbitrary and discrete amounts. At each assumed diameter of the central hole in the Vertical Release Lever, the Vertical Release Lever was rotated around the axis of rotation until it made contact with the Vertical Shaft. The angle between the Vertical Release Lever and the Central Shaft at each point of contact was calculated in SolidWorks and reported here as the Angle of Rotation.

Results

Table 1 below lists the data points and the corresponding calculated Angles of Rotation. Diameters are measured in inches, angles are measured in degrees.

TABLE 1

Calculated Angle of Rotation as a Function of Hole/Shaft Diameter

| Data Point | Central Hole in The Vertical Release Lever Diameter | Vertical Shaft Outer Diameter | Difference | Calculated Angle of Rotation |
|---|---|---|---|---|
| 1 | 0.500 | 0.500 | 0.000 | 0.00 |
| 2 | 0.502 | 0.500 | 0.002 | 0.94 |
| 3 | 0.505 | 0.500 | 0.005 | 2.24 |
| 4 | 0.507 | 0.500 | 0.007 | 3.04 |
| 5 | 0.510 | 0.500 | 0.010 | 4.16 |
| 6 | 0.512 | 0.500 | 0.012 | 4.88 |
| 7 | 0.517 | 0.500 | 0.017 | 6.55 |

It is evident from the data in Table 1 that as the diameter of the central hole in the Vertical Release Lever increases relative to the diameter of the Vertical Shaft, the Vertical Release Lever is able to rotate through a larger angle.

Of note, Data Point 1 describes a dimensional condition where the diameters are identical. This condition allows no movement of the Vertical Locking Lever and therefore is non-functional in practice. It is included here because it illustrates a theoretical extreme in the dimensional relationships.

Of further note, Data Point 4 is the dimensional condition that is present in the existing functional prototype models, and represents a known, functional geometry. In order to develop a general relationship (one that is not necessarily dependent on a specific dimension or system of measurement units) we can normalize this dimensional data by dividing all diameters by the Vertical Shaft diameter and subtracting unity. For example, the normalized outer diameter of the Vertical Shaft is (0.500/0.500)−1=1.000−1=0.000. Further, the Central Hole diameter in Data Point 2 is normalized as (0.502/0.500)−1=1.004−1=0.004. The result is a dimensionless diameter as listed in Table 2.

TABLE 2

Calculated Angle of Rotation as a Function of Normalized Hole/Shaft Diameter.

| Data Point | Central Hole in the Vertical Release Lever Diameter, Normalized to Shaft Diameter | Calculated Angle of Rotation |
|---|---|---|
| 1 | 0.000 | 0.00 |
| 2 | 0.004 | 0.94 |
| 3 | 0.010 | 2.24 |
| 4 | 0.014 | 3.04 |
| 5 | 0.020 | 4.16 |
| 6 | 0.024 | 4.88 |
| 7 | 0.034 | 6.55 |

Figure 11:
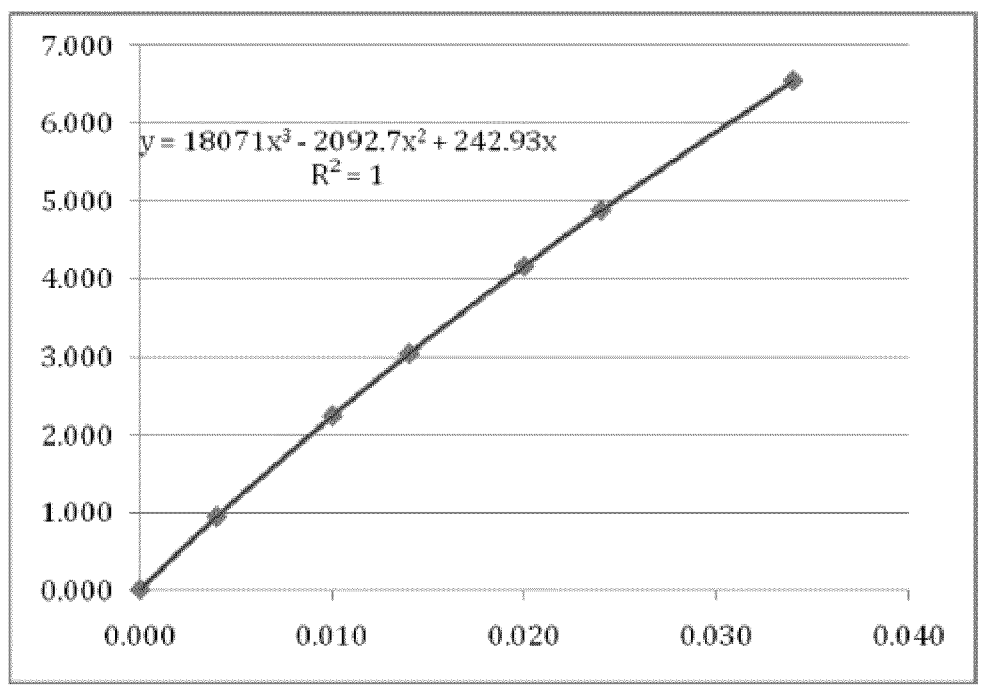
FIG. 11 is a graph illustrating a calculated angle of rotation as a function of normalized hole/shaft diameter.

The relationship may be plotted as indicated in FIG. 11, which is a graph illustrating the calculated angle of rotation as a function of normalized hole/shaft diameter.

A regression equation may be obtained to describe the relationship. The form of this regression equation may be any convenient form that adequately describes the relationship. We find that using a least square fit through the calculated and normalized data points a third order polynomial equation of the form $y=b+c_1 x+c_2 x^2+c_3 x^3$ fits the data with an R-square valve (where R is the Pearson product moment correlation coefficient) equal to 1. This regression equation is found to be:

$$y=18071 x^3 - 2092.7 x^2 + 242.93 x \qquad \text{(Eq. 1)}$$

Equation 1 is a generalized relationship describing the rotation of the Vertical Release Lever around a circular Vertical Shaft for a range of normalized diameter differences for the subject geometry.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A carriage holder for support of an apparatus comprising:
   identical upper and lower support plates having on their outer edge a number of indentations corresponding to the number of apparatus to be supported, said indentations providing aligned radial horizontal grasping surfaces on one side of said carriage holder;
   a series of vertical spring pivot pins joining said upper and lower support plates, adjacent to each said indentation, each such pin bearing a torsion spring loaded retractable clamp member to provide grasping surfaces in retracted position opposite to the grasping surfaces of said indentations;
   an unobstructed aperture in each of said aligned support plates for mounting said carriage holder on a shaft; and
   a locking mechanism to hold said carriage in a fixed position on the shaft.

2. A locking mechanism to hold a platform plate in an adjustable fixed position on a shaft comprising:
   a locking lever having a handle and body portion containing an aperture larger than a diameter of the shaft to fit over the shaft, tabs located laterally between said aperture and said handle, and bores on either side of the locking lever aperture through which stabilizing pins are disposed to guide a force mechanism applied in orientation to the locking lever to maintain it in locked position; and
   mounting blocks affixed to said platform plate on either side of said locking lever containing bushings to accommodate said tabs of said locking lever thereby providing an axis of rotation to said lever, the locking position occurring when the rim of said aperture is rotated by said force mechanism into a contact engagement zone with the shaft.

3. The carriage holder of claim 1, wherein said torsion spring is anchored by extension of a spring wire to a loop engaging a stationary post to prevent rotation of the spring.

4. The locking mechanism of claim 2, wherein the force mechanism comprises one or more of a solenoid, a hydraulic or pneumatically activated piston, and a spring.

5. The locking mechanism of claim 2, wherein the force mechanism is configured to apply a force to prevent slippage of the locking mechanism given the weight bearing load of the platform, wherein the force does not impede axial rotation of said platform about the shaft.

6. The carriage holder of claim 1, wherein said locking mechanism comprises:
   a locking lever having a handle and body portion containing an aperture larger than a diameter of the shaft to fit over the shaft, tabs located laterally between said aperture and said handle, and bores on either side of the aperture through which stabilizing pins are disposed to guide a force mechanism applied in orientation to the locking lever to maintain it in locked position; and
   mounting blocks affixed on either side of said locking lever containing bushings to accommodate said tabs of said locking lever thereby providing an axis of rotation to said lever, the locking position occurring when the rim of said aperture is rotated by said force mechanism into a contact engagement zone with the shaft.

* * * * *